(12) United States Patent
Moenning et al.

(10) Patent No.: US 8,282,589 B2
(45) Date of Patent: Oct. 9, 2012

(54) RESTRAINT DEVICE AND METHOD OF USE

(75) Inventors: Stephen P. Moenning, Punta Gorda, FL (US); Anne E. Moenning, Punta Gorda, FL (US)

(73) Assignee: Collar ID, LLC, Punta Gorda, FL (US)

( * ) Notice: Subject to any disclaimer, the term of this patent is extended or adjusted under 35 U.S.C. 154(b) by 0 days.

(21) Appl. No.: 13/252,561

(22) Filed: Oct. 4, 2011

(65) Prior Publication Data

US 2012/0029403 A1     Feb. 2, 2012

Related U.S. Application Data

(63) Continuation of application No. 13/021,311, filed on Feb. 4, 2011, now Pat. No. 8,057,416, which is a continuation of application No. 11/461,559, filed on Aug. 1, 2006, now Pat. No. 7,883,485.

(60) Provisional application No. 60/742,835, filed on Dec. 6, 2005, provisional application No. 60/704,367, filed on Aug. 1, 2005.

(51) Int. Cl.
*A61F 5/00* (2006.01)
(52) U.S. Cl. .................................. 602/18; 128/DIG. 23
(58) Field of Classification Search ................... 602/1, 5, 602/17–19, 32–35; 128/DIG. 23
See application file for complete search history.

(56) References Cited

U.S. PATENT DOCUMENTS

| | | |
|---|---|---|
| 2,162,984 A | 6/1939 | Thomas |
| 3,117,608 A | 1/1964 | Goss et al. |
| 3,147,607 A | 9/1964 | Calvano et al. |
| 3,818,897 A | 6/1974 | Smith |
| 4,226,036 A | 10/1980 | Krug |
| 4,811,844 A | 3/1989 | Moulding, Jr. et al. |
| 4,947,867 A | 8/1990 | Keeton |
| 5,038,759 A | 8/1991 | Morgenstern |
| 5,215,517 A | 6/1993 | Stevenson et al. |
| 5,531,669 A | 7/1996 | Varnau |
| 5,568,951 A | 10/1996 | Morgan |
| 6,027,149 A | 2/2000 | Kosky |
| 6,036,664 A | 3/2000 | Martin, Sr. et al. |
| 6,109,673 A | 8/2000 | Olshausen |
| 6,409,237 B1 | 6/2002 | Olshausen |
| 6,423,020 B1 | 7/2002 | Koledin |
| 6,663,581 B1 | 12/2003 | Calabrese |
| 7,198,190 B2 | 4/2007 | Juhan et al. |
| 7,371,221 B1 | 5/2008 | Baker |
| 2004/0015117 A1 | 1/2004 | Gauthier |
| 2004/0111942 A1 | 6/2004 | Stonehocker |
| 2005/0101896 A1 | 5/2005 | Calabrese |

*Primary Examiner* — Patricia Bianco
*Assistant Examiner* — Tarla Patel
(74) *Attorney, Agent, or Firm* — Wood, Herron & Evans, L.L.P.

(57) ABSTRACT

A restraint device includes first and second restraint and/or support portions adapted to extend around part of a person. First and second connector portions may secure the first and second restraint and/or support portions to the person. A lock member may be used to selectively prevent disconnection of the first and second connector portions. One or more removable tags or other information elements may be carried on at least one of the first and second restraint and/or support portions and may indicate who placed the restraint device on, or removed the restraint device from the person, and/or what time the restraint device was placed or removed. The tags or other elements may include a unique identifier to indicate whether the restraint device had been previously removed from the person after an initial placement. The restraint device may include an electronic information element configured to transmit information related to the wearer.

22 Claims, 11 Drawing Sheets

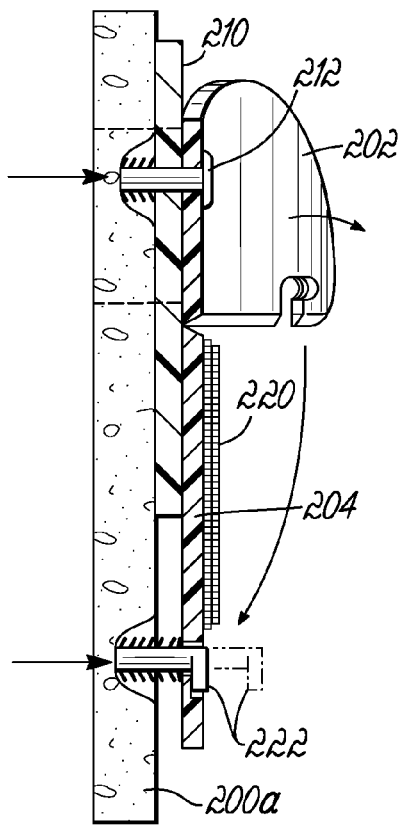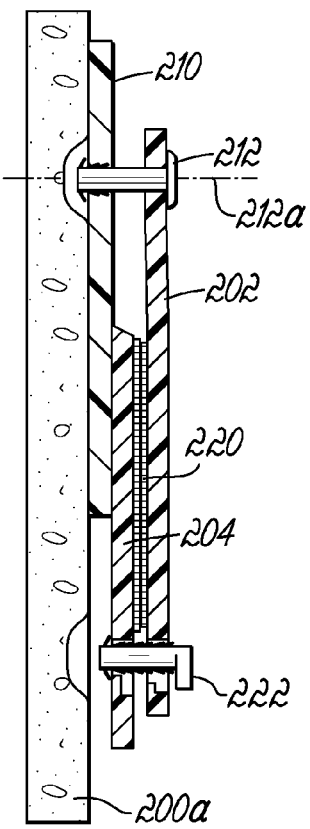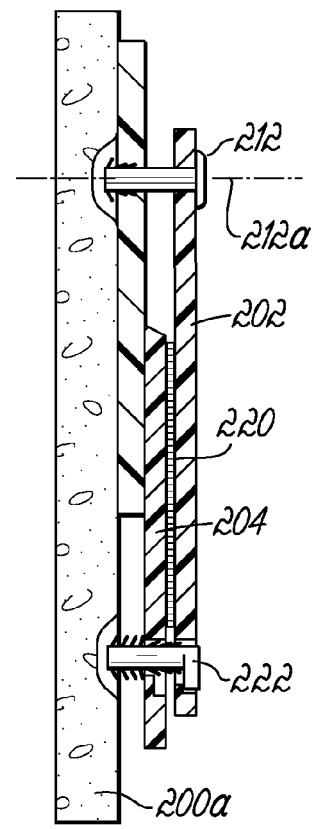
FIG. 9A     FIG. 9B     FIG. 9C
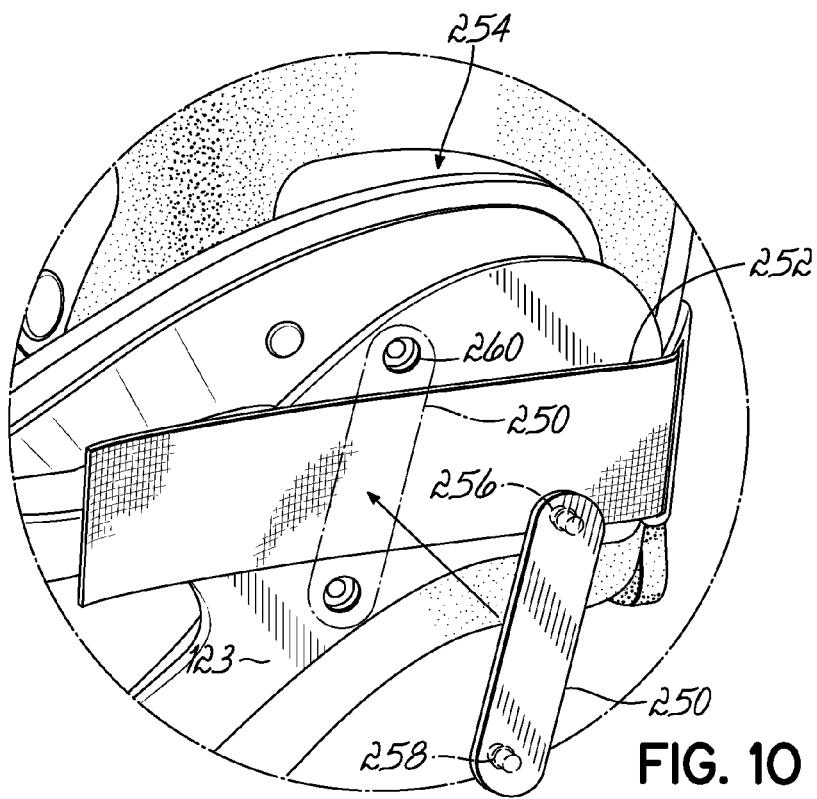
FIG. 10

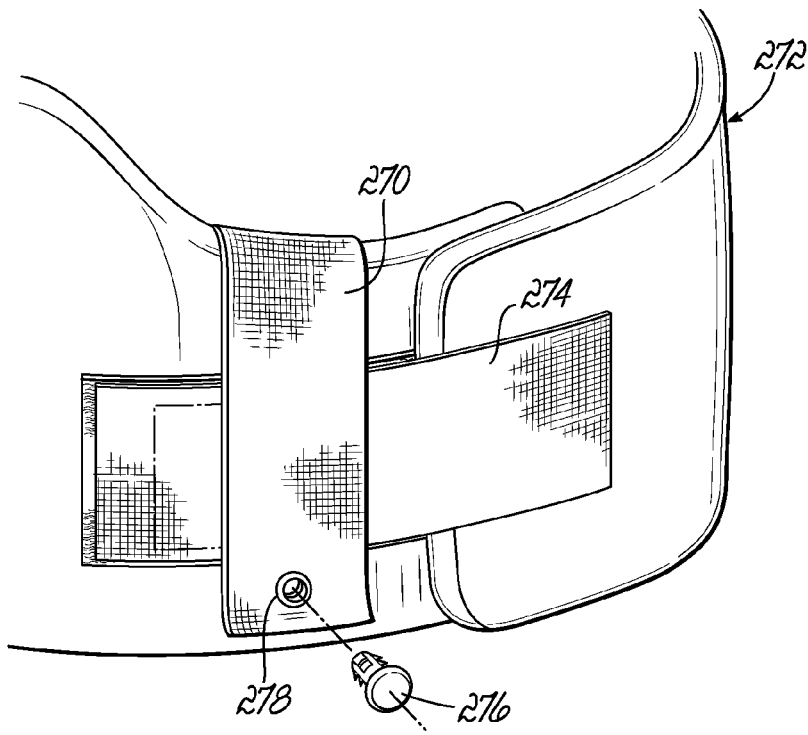
FIG. 11
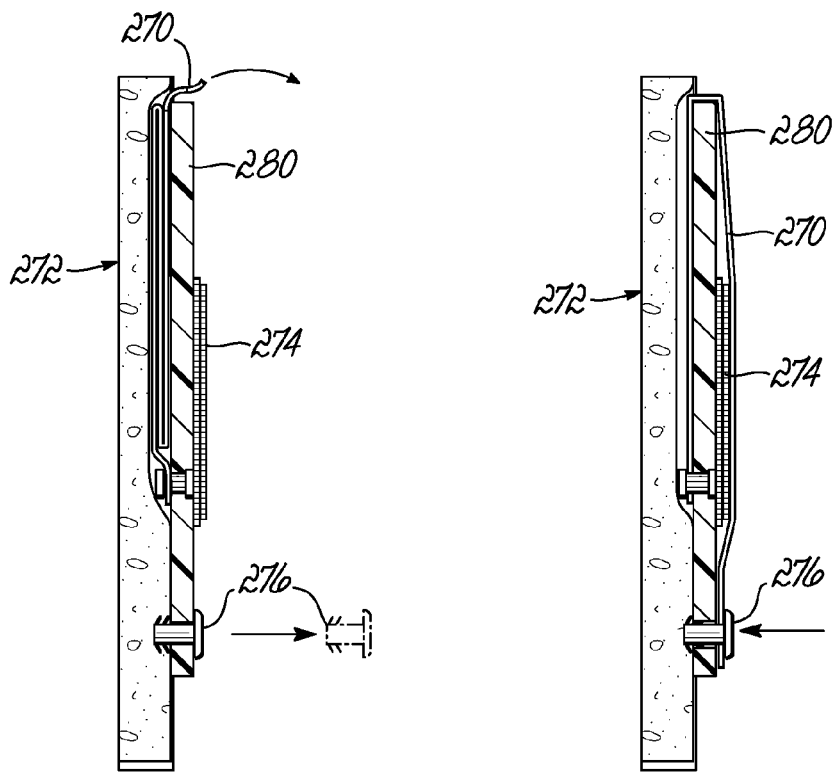
FIG. 12A  FIG. 12B

RESTRAINT DEVICE AND METHOD OF USE

CROSS REFERENCES

This application is a continuation of U.S. patent application Ser. No. 13/021,311 filed Feb. 4, 2011 which is a continuation of U.S. patent application Ser. No. 11/461,559 filed Aug. 1, 2006 (now U.S. Pat. No. 7,883,485), which claims the benefit of U.S. Provisional Patent Application Ser. Nos. 60/704,367 and 60/742,835, respectively filed on Aug. 1, 2005 and Dec. 6, 2005, the disclosures of which are expressly incorporated by reference herein in their entirety.

TECHNICAL FIELD

The present invention generally relates to body restraints, such as cervical collars used to immobilize or brace the head and neck region of a patient or other restraining devices for immobilizing or preventing unwanted movements of one or more body portions of a person such as a patient, etc.

BACKGROUND

Cervical collars have been used for many years to immobilize or brace the head and neck region of patients who have undergone head or neck trauma, or who are at risk for spinal cord injuries should the head or neck of the patient be moved prior to either full diagnosis or treatment by a physician. For example, many trauma patients of automobile accidents or other types of accidents are treated by emergency medical professionals in the field and, as either a necessary or precautionary course of treatment, the field technician may apply a cervical collar to the victim at least until the time that an emergency room physician or other physician determines that the patient is no longer at risk for spinal cord injury should the cervical collar be removed. Typically, the cervical collar is comprised first and second halves which are generally semicircular in shape and fit around respective front and rear portions of the patient's neck. These two halves are secured together by straps which typically incorporate hook and loop fastening material for quick, easy and yet secure attachment of the straps to each other. When it is desired to remove the cervical collar from the patient, straps on one or both sides of the collar are disconnected by simply pulling the straps away from the collar to disengage the hook and loop fastening material.

Unfortunately, the ease with which a cervical collar may be removed from a patient and/or the inability to determine who removed the collar and/or what time the collar was removed, can create problems leading to premature removal of cervical collars from patients. This can result in spinal cord injury or other injury to the patient. For example, emergency room medical personnel may remove the collar prior to obtaining approval from the physician in charge of the patient. Whether such emergency room personnel remove the collar due to simply mistaken belief that approval to do so has been obtained, or in disregard of proper protocol, avoidable injuries to the patient may be the result. In other situations, it may be the patient himself, or a member of the patient's family, or an acquaintance of the patient that removes the collar for any of a variety of reasons. The patient, for example, may be belligerent such as in the case of a trauma patient that was involved in a vehicle accident while driving under the influence. In such a case, the patient may be generally uncooperative and this may include attempts at removing any restraining devices, including their cervical collar.

A report by The Institute of Medicine entitled "To Err Is Human: Building a Safer Health System" estimates that 44,000 patients die each year due to medical errors. Some studies place the number of deaths as high as 98,000. Total national costs (e.g., lost income, production, disability, etc.) as a result of medical errors are estimated to be between $17 billion and $29 billion. Of this amount, almost half is healthcare costs. Cervical collar safety is one important area to address.

As the healthcare system continues to experience growth, issues of communication will continue to be a challenge for all healthcare workers. For example, in the field of acute cervical collar application, when a cervical collar is placed by a medic in the field, few if any mechanisms are in place for assuring that the medic will accurately communicate with a subsequent healthcare worker regarding the time that the patient received the cervical collar. Factors that contribute to impaired communication between healthcare workers may include, but are not limited to, differences between technical specialties (EMT medic vs. nurse), gender related issues (male v. female), hierarchical issues (trauma surgeon v. nurse) and corporate issues (healthcare worker v. hospital corporation). Other issues influencing communication and documentation of application of the cervical collar include the method of documentation in the patient's chart. Some healthcare workers may always document application and/or removal of the cervical collar and some workers may not document application/removal of the collar at all. If an error occurs resulting in neurological injury, and the collar is off the patient, liability might be placed on any of those individuals involved with the care of that patient. This results in greater financial stress on an already burdened healthcare system.

In the field of chronic cervical care, there is also a need for healthcare workers to communicate the removal and application of the collar. Frequently, cervical collars must be left on a patient for prolonged periods of time to stabilize the neck. As the cervical collar is left in place for long periods of time, a healthcare worker must clean under the collar and ensure that there is no skin breakdown. Current cervical collar technology does not afford a standardized way to document that the collar has been removed, the skin has been inspected, and collar has been reapplied.

A device is needed to help minimize medical errors involving the placement and removal of a cervical collar in both the acute and chronic care states. Such a device could encourage communication among various healthcare workers, with regard to a cervical collar placement. What is needed is a device that will standardize the application and removal of a cervical collar, thereby lowering the possibility of medical errors. Whether cervical collar care is provided in the emergency room or the nursing home, what is needed is a cervical collar designed as a support system for cervical collar communication between healthcare workers and the healthcare system.

In view of at least the above-mentioned issues, it would also be desirable to provide improvements that help ensure that cervical collars are only removed when an appropriate medical professional has determined that doing so would not unnecessarily risk additional injury to the patient. It would also be helpful to know if the cervical collar has been inappropriately removed or tampered with while on the patient. Various other challenges exist with regard to any number of restraint devices.

SUMMARY

The present invention, in one general aspect, provides a cervical collar comprising a first support portion configured to extend around and support a first portion of the neck of a patient. A second support portion of the cervical collar is configured to extend around and support a second portion of the neck of the patient. In all of the embodiments, the support portions may be separate pieces or components or portions of the same piece or component. A first connector portion is coupled with the first support portion, and a second connector portion is coupled with the second support portion. The first and second connector portions have respective first and second coupling members capable of being selectively connected together to secure the first and second support portions around the first and second portions of the neck of the patient and disconnected to release the first and second support portions from around the first and second portions of the neck of the patient. A lock member is coupled to at least one of the first and second support members and is configured to selectively prevent the first and second coupling members from being disconnected in a manner that would allow the release of the first and second support portions from around the first and second portions of the neck of the patient.

The first connector portion may further comprise a strap and the first coupling member may further comprise one of a hook and loop fastening material. The other coupling member would then comprise the other of the hook and loop fastening material. The lock member may further comprise a tie that includes a one way fastening mechanism adapted to allow the tie to be configured into a loop. The loop may, for example, then extend transversely across one of the straps that serve as a connector portion such that the strap may not be pulled and completely disconnected from the mating strap or other connector portion. At least one of the first and second support portions may include a grommet member generally adjacent at least one of the first and second connector portions through which the lock member may extend. In another aspect, a cutting mechanism may be coupled with at least one of the first and second support portions and configured to cut the lock member to allow the first and second coupling members to be disconnected.

In another aspect of the invention, which may or may not be used in conjunction with the use of a lock member on the cervical collar, a removable tag or other information element may be carried on at least one of the first and second support portions. This type of element may be used to indicate at least one of, for example: 1) who placed the cervical collar on a patient; 2) who removed the collar from the patient; 3) what time the collar was placed on the patient; and 4) what time the collar was removed from a patient. Information elements such as bar code elements, RFID elements, fingerprint patches or other machine-readable elements may be used. Still others include voice chips or any other information element capable of at least assisting with the recordation of the desired information. Other information that such elements may give can relate to location of the collar. For example, any electronic locating technology (e.g., global positioning system or GPS) may be used and incorporated into the collar or other restraint device of this invention.

Multiple, single use lock members may be carried on at least one of the first and second support portions. In this manner, when a first lock member has been cut off of the cervical collar, for example, and the cervical collar needs to be used again, a second single use lock member may be taken from a suitable location on the collar and used once again to lock the connector portions in place. As another aspect, each of the single use lock members may have a unique identifier to indicate to a medical professional whether or not the collar has been removed from a patient after initial placement on the patient. For example, a color-coded system may be used whereby a first dispensed lock member is colored red, a second single use lock member is colored orange and a third single use lock member is colored yellow. In this manner, if the orange lock member is secured in place over the connector portions, then this establishes that the red lock member had already been used and cut off the collar. Therefore, the collar had presumably been removed from the patient and reapplied and locked using the orange lock member. This concept may be more broadly applied to the collar by simply utilizing a plurality of removable tags carried on at least one of the first and second support portions. Each of the removable tags would likewise have a unique identifier to indicate to a medical professional whether or not the collar had been removed from the patient after initial placement on the patient. The unique identifier could, for example, comprise a different color on each of the removable tags. These tags may or may not also include additional information input by a medical professional such as the time that the collar was applied to and/or removed from the patient, and/or the name of the individual that applied the collar and/or removed the collar.

The invention further contemplates various methods of attaching and, optionally, locking a cervical collar to a patient. In one method, the first support portion is secured around a first portion of the neck of the patient. A second support portion of the cervical collar is secured around a second portion of the neck of the patient. A first connector portion is secured or fastened to a second connector portion in order to securely couple the first and second support portions of the collar to the neck of the patient thereby securely immobilizing the neck of the patient. A lock member is secured to selectively prevent the first and second connector portions from being disconnected in a manner that would allow the release of the first and second support portions from around the first and second portions of the neck of the patient. The lock member may be part of a manually operable mechanical locking system.

In another aspect, a method of attaching a cervical collar to a patient comprises securing a first support portion of the cervical collar around a first portion of the neck of the patient. A second support portion of the cervical collar is then secured around a second portion of the neck of the patient. A first connector portion coupled with the first support portion is fastened to a second connector portion coupled with the second support portion to securely couple the first and second support portions to the neck of the patient thereby securely immobilizing the neck of the patient. Using an information element associated with the collar, the method further comprises indicating at least one of: 1) who placed the cervical collar on a patient, and 2) what time the collar was placed on the patient. The method may further comprise indicating on an information element associated with the collar at least one of: 1) who removed the collar from the patient, and 2) what time the collar was removed from the patient.

In another aspect, a method of attaching a cervical collar to a patient comprises securing a first support portion of the cervical collar around a first portion of the neck of the patient. A second support portion of the cervical collar is then secured around a second portion of the neck of the patient. A first connector portion coupled with the first support portion is fastened to a second connector portion coupled with the second support portion to securely couple the first and second support portions to the neck of the patient thereby securely immobilizing the neck of the patient. Using an element associated with the collar, the method further comprises indicating whether the collar was previously removed from the patient. As mentioned above, this may include indicating removal of the collar using color-coded elements associated with the collar.

In another aspect, various portions of the collar may be formed from or have high visibility features such as fluorescent, reflective, luminescent, and/or glow in the dark material or characteristics to facilitate greater visibility to a user. For example, one or more portions of the lock system and/or information elements may be formed from materials having one or more of these high visibility features, or may otherwise be modified to have one or more of these high visibility features. The removable tags may also have one or more of these high visibility features. This would, for example, allow a user to more readily see and manipulate the removable tags, lock system, etc. before, during or after applying or removing the collar.

In another aspect of the invention, a lock and/or identifier (e.g., tag) system may be placed onto an existing conventional collar allowing one or more of the methods described herein to be performed with respect to existing, conventional collars without modifying the collar itself during manufacture thereof to include one or more of the inventive features discussed herein.

In another aspect of the invention, a restraint device for limiting movement of a wearer, such as a cervical collar or a restraint device for use in security or law enforcement applications, may include at least one electronic information element associated with the restraint device. The electronic information element may be configured to transmit information related to the wearer of the restraint device. The restraint device may additionally or alternatively be configured to record information related to the wearer of the restraint device.

Any of the features disclosed herein may be incorporated into any restraining device adapted to restrict unwanted movements of a body of a person. Such persons may or may not be patients of medical professionals. For example, they may instead be detainees of law enforcement officials.

These and other features, objects and advantages of the invention will become more readily apparent to those of ordinary skill in the art upon review of the following detailed description, taken in conjunction with the accompanying drawings.

BRIEF DESCRIPTION OF DRAWINGS

FIGS. 9A-9C are cross sections generally taken along line 9A-9A of FIG. 8A and showing the operation of the pop-out, pivoting lever.

FIG. 10 is an enlarged view similar to FIG. 8B, but showing another type of lock member that may be snapped or otherwise fastened into place across the connector strap of the collar.

FIG. 11 is a perspective, partially fragmented view of a collar with another alternative lock in the form of a strap that may be applied transversely across one of the connector straps of the collar and fastened into place with a push fastener.

FIGS. 12A and 12B are cross sections showing that the strap of FIG. 11 may be stored in a concealed location as shown in FIG. 12A, and pulled out and fastened across the connector strap of the collar as shown in FIG. 12B.

DETAILED DESCRIPTION OF ILLUSTRATIVE EMBODIMENTS

Figure 1:
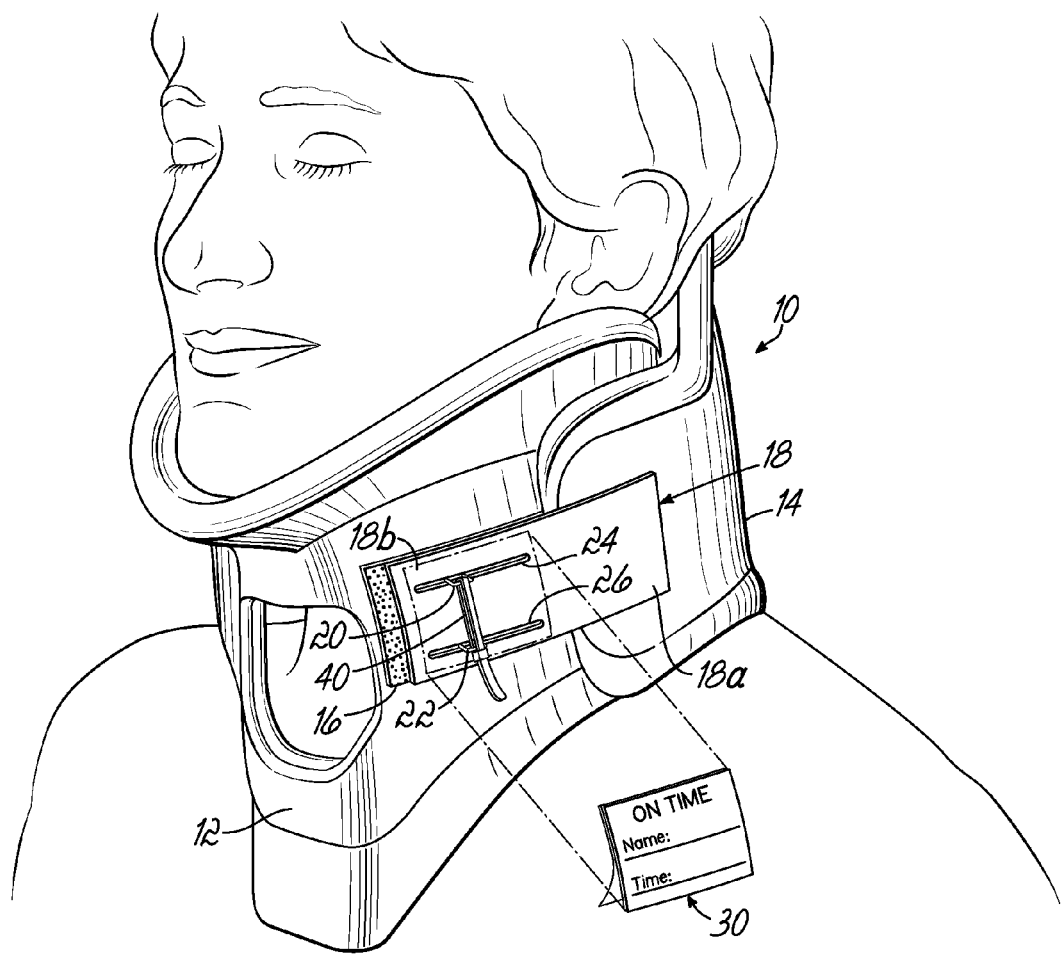
FIG. 1 is a perspective view of a patient wearing a cervical collar constructed in accordance with a first embodiment of the invention.

FIG. 1 illustrates a patient wearing a cervical collar 10 constructed in accordance with one illustrative embodiment of the invention. The cervical collar 10 includes first and second support portions 12, 14 configured to immobilize, or at least brace the patient's head and neck region. In regard to the illustrative collar 10, support portions 12, 14 are respective halves of the collar 10, however, other numbers of support portions may be used instead. Such cervical collars may have any number of design characteristics and the cervical collars illustrated herein are simply representative in nature. The cervical collar 10 may be formed of many different types of materials, and include many different types of design features and capabilities. It is to be understood that the inventive concepts discussed and claimed herein may be applied to all types of cervical collars including one-piece collars having the requisite support portions adapted to be wrapped around a patient's neck. In this case, the "support portions" will be respective parts of a single wrap-around structure. Alternatively, multi-piece collars may be used in which the support portions are comprised of separate pieces brought together around a patient's neck. The illustrated cervical collar 10 includes first and second halves 12, 14, which comprise front and rear halves of the collar 10, coupled by a strap system or connector system. In the illustrated embodiment of FIG. 1, a first connector portion 16 is secured to the front half of the collar 10, and the rear half of the collar includes a mating strap 18 having one end 18a securely fastened to the rear half of the collar 10 and another free end 18b extendable over the connector portion 16 coupled with the front half of the collar 10. The strap 18 and connector portion 16 have coupling members which, in this illustration, comprise mating hook and loop fasteners. The strap 18 may have the hook portion of the fastener and the connector portion 16 on the front half of the collar 10 may have the loop portion of the fastener, or vice versa.

Figure 2A:
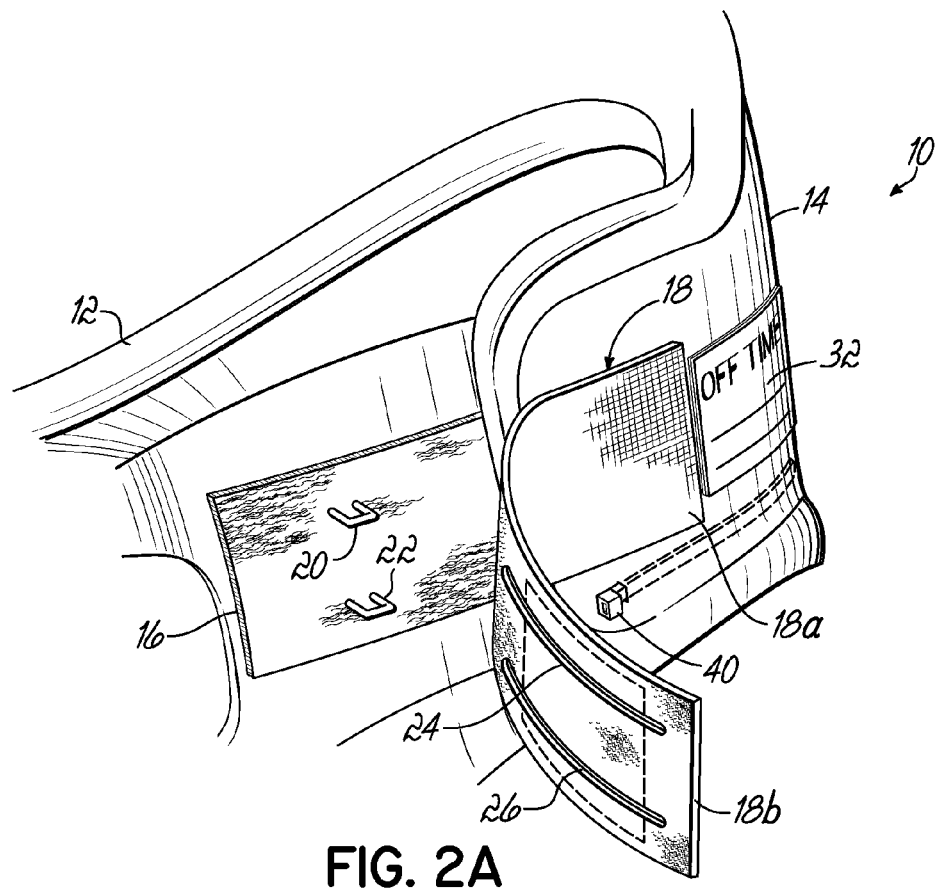
FIG. 2A is an enlarged perspective view of the collar shown in FIG. 1, illustrating the strap of one support portion of the collar disconnected from a connecting portion on another support portion of the collar.
Figure 2B:
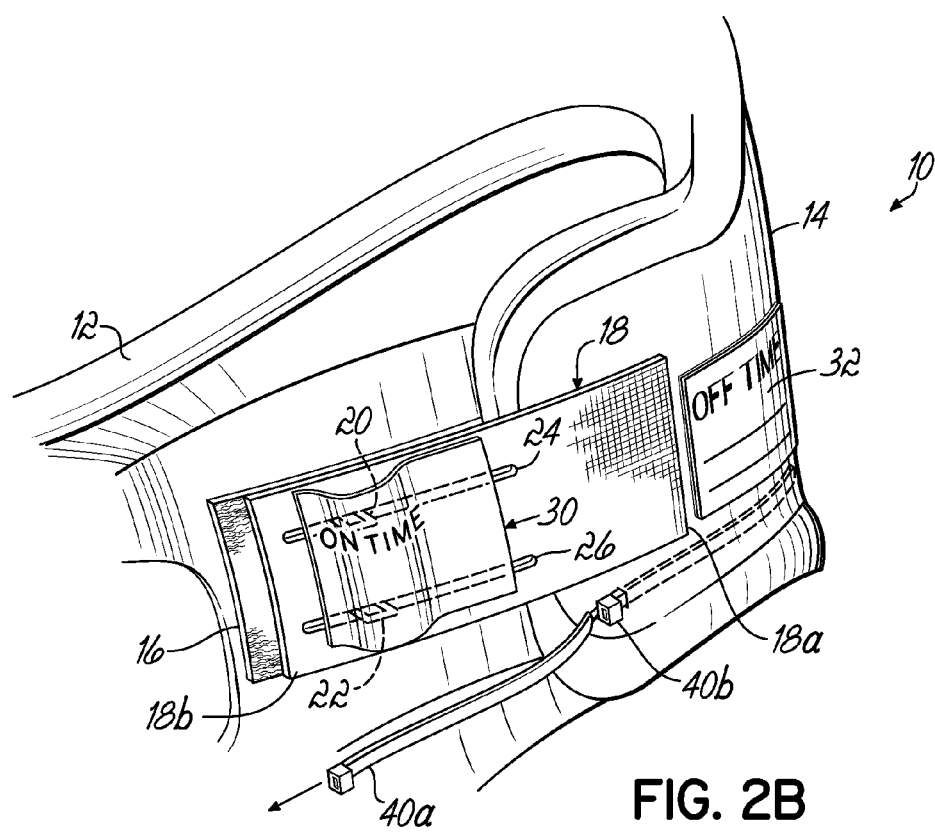
FIG. 2B is a perspective view similar to FIG. 2A, but illustrating the two support portions of the collar connected together.
Figure 2C:
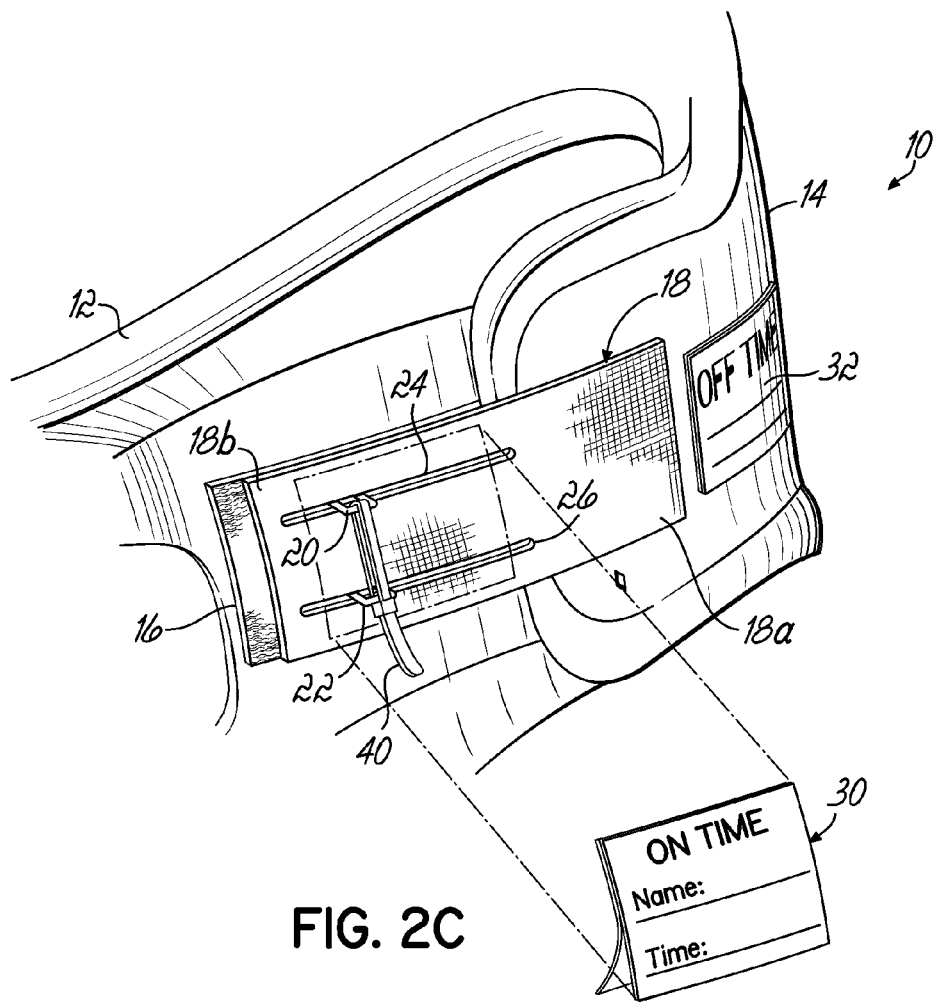
FIG. 2C is a view similar to FIG. 2B, but illustrating a locked condition of the collar.

Referring now to FIGS. 1, and 2A-2C, a pair of grommets 20, 22 are securely fastened to the front half of the collar 10 and extend from the support portion 12. These grommets 20, 22 are extendable through respective slots 24, 26 in the strap when the strap 18 is laid over the connector portion 16. Thus, the collar 10 may be placed on the patient, and then the strap 18 may be placed over the connector 16 portion such that each slot 24, 26 receives a respective grommet 20, 22 (as shown in phantom lines in FIG. 2B). This pushes an identification tag 30 away from the strap 20 forcing the person applying the collar 10 to take the tag 30 off the strap 20 and prompting them to write their name on the tag 30 and the time that the collar 10 was applied to the patient. Removal of the tag 30 exposes the grommets 20, 22 such that a suitable lock member 40, such as a zip tie or other type of locking member, may be extended through the grommets 20, 22 and locked in place as shown in FIG. 2C. This prevents the strap 18 from being pulled fully away from the underlying connector portion 16. Therefore, to remove the collar 10, the lock member 40 (or zip tie in this case) must first be removed, as by cutting the tie 40 with a pair of scissors (not shown), before the strap 18 may be fully pulled away from the underlying connector portion 16 such that the two collar halves 12, 14 may be removed from the patient. As further shown in FIG. 2B, lock members 40a, 40b may be serially dispensed in a suitable manner from a location on the collar 10, such as by retaining multiple single-use lock members 40a, 40b in a pocket of the collar, or otherwise integrating the single use lock members with the collar so that they are used one at a time in a predetermined sequence. In this manner, for example, a first lock member 40a or tie may be colored red, a second lock member 40b or tie may be colored orange, a third lock member (not shown) may be colored yellow, etc. Therefore, if the orange lock member 40b is secured in place on the collar 10 which is applied to the patient, this likely means that the red lock member 40a, which was previously dispensed and presumably used, was cut off and the collar was removed from the patient and then reapplied and locked using the second single use lock member 40b. These lock members 40a, 40b may be coupled together such that a small amount of force will allow the first lock member 40a to be quickly disconnected from the second lock member 40b which is still retained in place and ready for subsequent use. Of course, many other methods of integrating lock members into the collar will be recognized by those of ordinary skill in the art.

The tags 30, best shown in FIG. 2C, include both an "on time" set of tags 30 and an "off time" set of tags 32. These tags 30, 32 would be filled out by the personnel that apply the collar 10 and remove the collar 10 so as to identify the person that either applied the collar or removed the collar and also identifying the time of application or removal on the corresponding tag 30, 32. The filled out tags 30, 32, for example, may be maintained in the patient's chart at the hospital thereby serving as record of the application and removal of the collar 10 to and from the patient, as well as the personnel that carried out the application and/or removal of the collar 10, and/or the time of performing the application and/or removal procedures. It will be appreciated that other information elements may be used in place of or in conjunction with tags 30, 32. These elements may be more automated such as, but not limited to, bar code elements, RFID elements, voice chips, fingerprint patches, etc. Such elements may also include information related to the location of the collar 10. For example, this type of information element may be an electronic transmitter and/or receiver, or other electronic element, that would help locate a patient, prisoner or other person that has left a hospital or other facility without authority or knowledge by those in charge. Various technologies may be used in this regard, such as GPS technology and the same element may be used in a number of different manners, including for information recording purposes and location identification purposes.

Figure 4A:
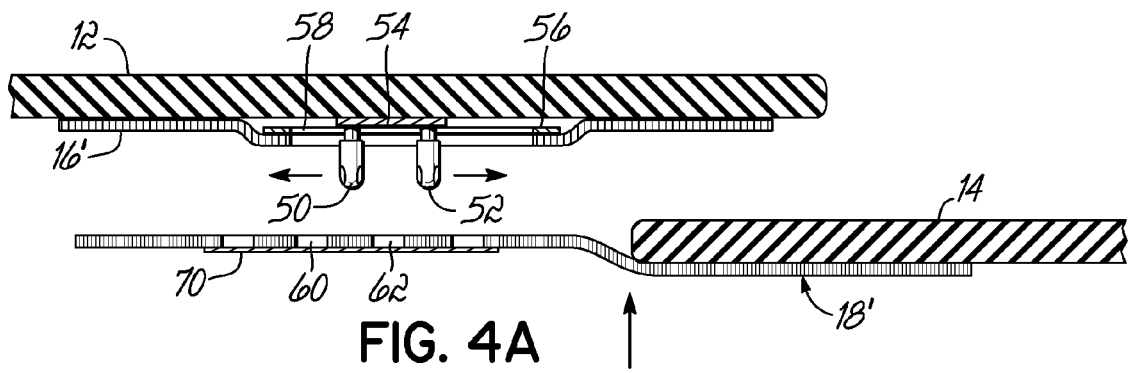
FIG. 4A is a cross sectional view generally taken along line 4A-4A of FIG. 3.
Figure 4B:
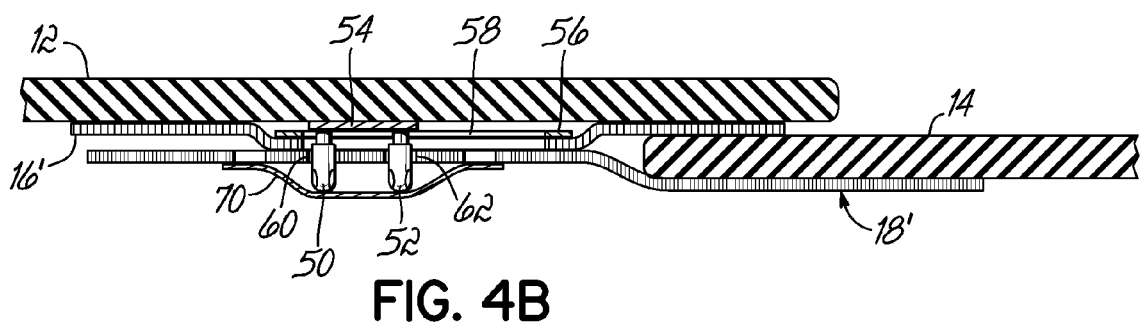
FIG. 4B is a cross sectional view similar to FIG. 4A, but showing the two support portions of the collar connected together, but unlocked.
Figure 4C:
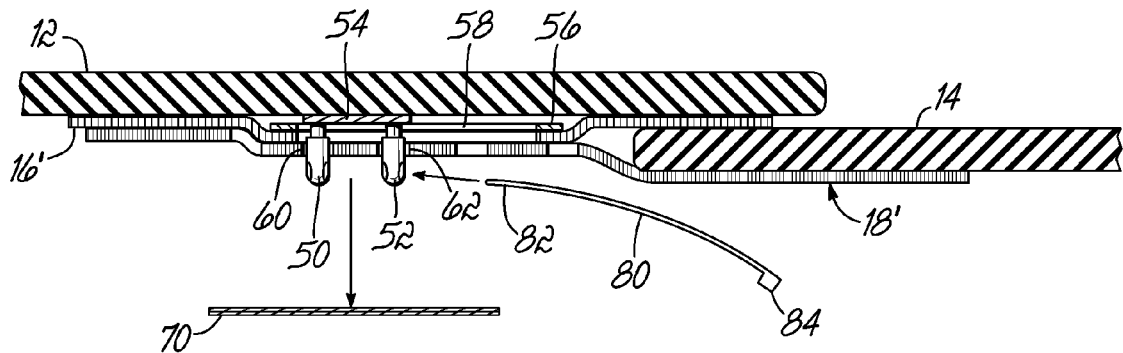
FIG. 4C is a cross sectional view similar to FIG. 4B, but illustrating the process of assembling the lock member to the collar.
Figure 4D:
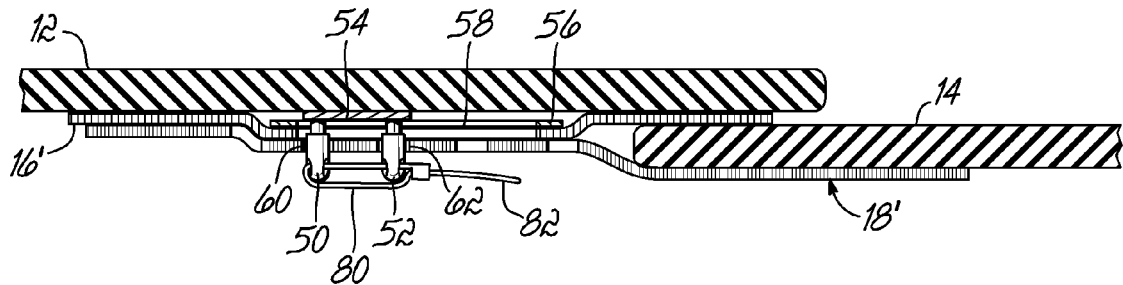
FIG. 4D is a cross sectional view similar to FIG. 4C, but illustrating the fully connected and locked condition of the collar.

FIGS. 3 and 4A-4D illustrate another embodiment of a lock system including adjustable grommets 50, 52 which are retained on a slide plate 54 beneath a holding plate 56. The grommets 50, 52 extend through a slot 58 in the holding plate 56 and may slide as a unit along the slot 58 to provide some adjustment. This adjustment allows the grommets 50, 52 to line up with a pair of slots or holes 60, 62 in the strap 18' as necessitated by any given patient or application. As shown in FIG. 4B, the grommets 50, 52 are lined up with the pair of holes 60, 62 in the strap 18' and pushed through the strap 18' thereby pushing a tag 70 away from the strap 18. This tag 70 may be an identification tag as previously discussed, which is filled out to identify the person applying the collar and/or the time of application. FIG. 4C illustrates the insertion of a lock member 80, such as a zip tie, through the grommets 50, 52 and FIG. 4D illustrates locking of the zip tie or lock member 80 into a loop configuration by inserting a free end 82 of the tie through a ratchet portion 84 of the tie 80. Therefore, to remove the lock member or tie 80 the tie 80 is cut between the grommets 50, 52 and the strap 18' may then be fully pulled away from the underlying connector portion 16.

Figure 5:
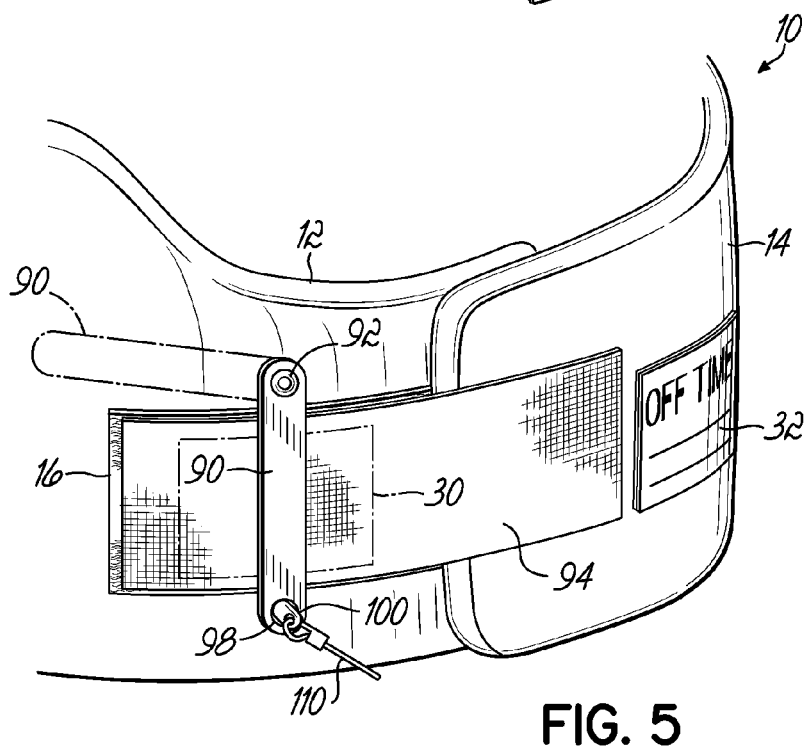
FIG. 5 is a perspective view illustrating the connector portions of the collar and an alternative locking system.
Figure 3:
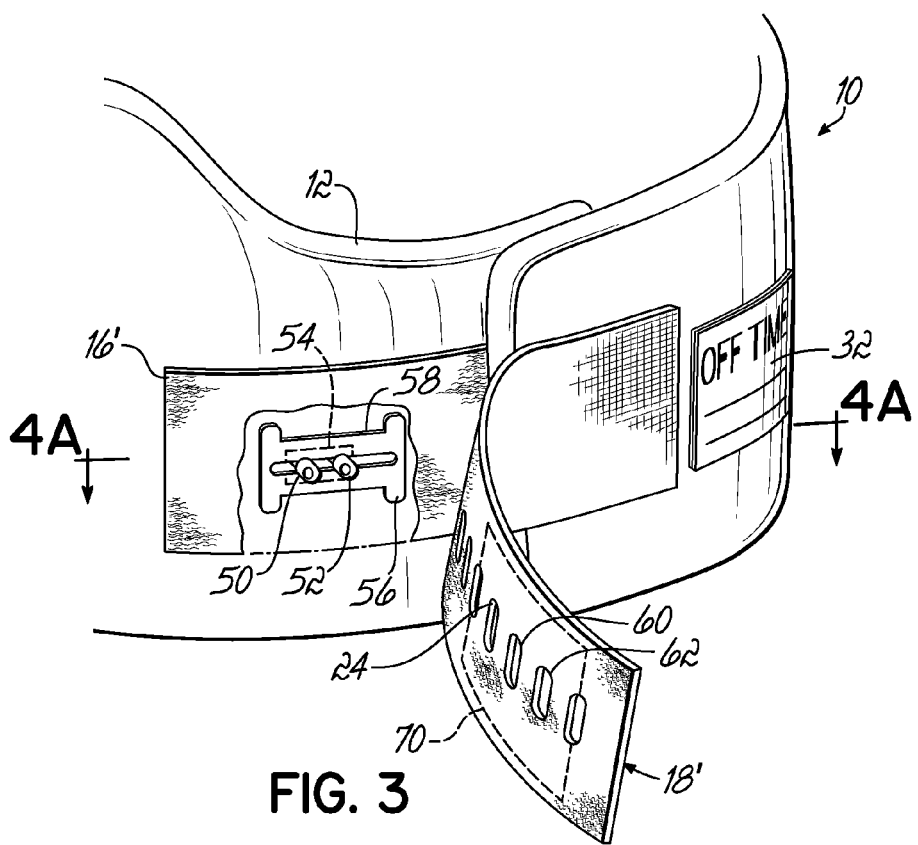
FIG. 3 is a view similar to FIG. 2A, but illustrating an alternative lock system for the collar.

FIG. 5 illustrates another alternative embodiment of a lock system in the form of a pivoting plate 90. This plate 90 may be fixed by a pivot 92 to one half 12 of the collar 10 and pivoted out of the way, such as shown in dash-dot lines so that a strap 94 may be applied to and removed from the underlying connector portion 96. When it is desired to lock the strap 94 in place and prevent full disconnection of the strap 94 from the underlying connector portion 96, the plate 90 may be pivoted over the strap 94 as shown in solid lines and a hole 98 in the plate 90 may be placed over a grommet or other suitable anchor member 100 which is fixed to the support portion or half 12 of the collar 10. A lock member 110, such as a zip tie, may then be fastened through the grommet or anchor 100, as shown, to lock the pivoting plate 90 in place. Again, when it is desired to unlock and remove the collar 10, the zip tie 110 may be cut or otherwise removed, and the pivoting plate 90 may be pivoted out of the way such that the strap 94 may be removed fully from the underlying connector portion 96.

Figure 6:
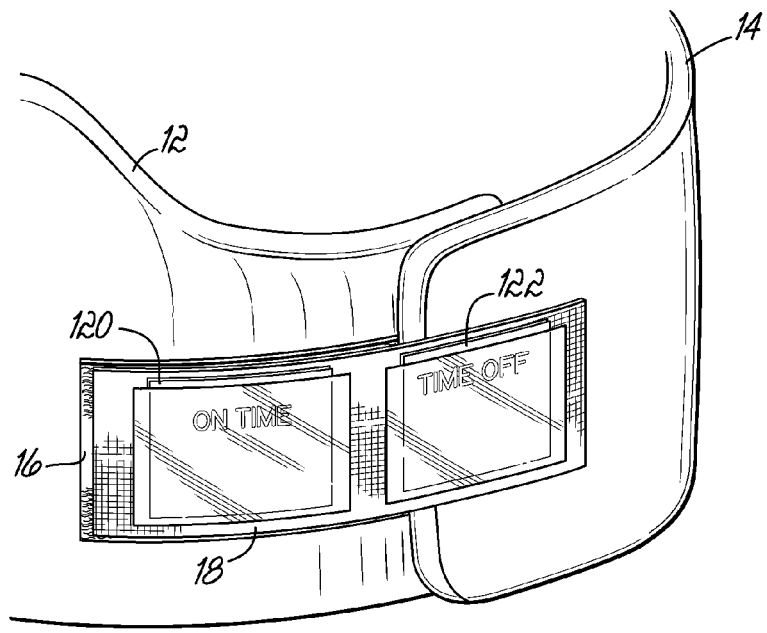
FIG. 6 is a perspective view similar to FIG. 5, but illustrating an alternative embodiment using identification tags.

FIG. 6 illustrates another embodiment in which the strap or connector system of the collar may be of any chosen design, and an identification tag system 120, 122 may be used generally as previously described. This tag system would more heavily rely on personnel dealing with the patient to record their identity when either applying the collar 10 or removing the collar and, optionally, or alternatively also recording the time of application or removal of the collar 10. In addition, or as another alternative, such tags 120, 122 may be simply color-coded and serially dispensed such that the color of the exposed tag would indicate how many times the collar had been applied and removed to that particular patient. For example, a first tag could be colored red, a second tag could be colored orange and a third tag could be colored yellow.

Figure 7A:
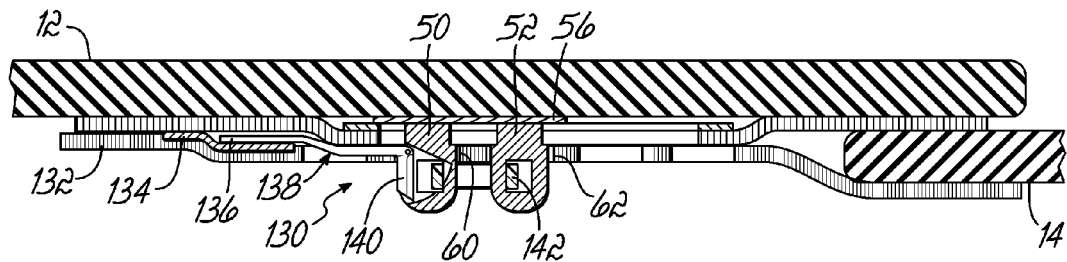
FIGS. 7A-7C are respective cross sectional views of an alternative connector region of the collar illustrating an integrated lock member cutting mechanism.
Figure 7B:
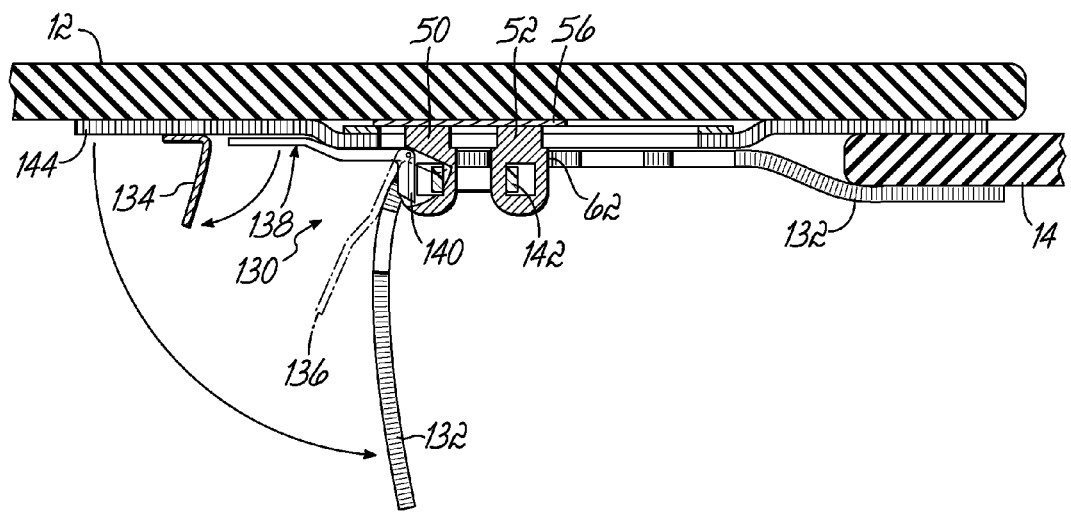
Figure 7C:
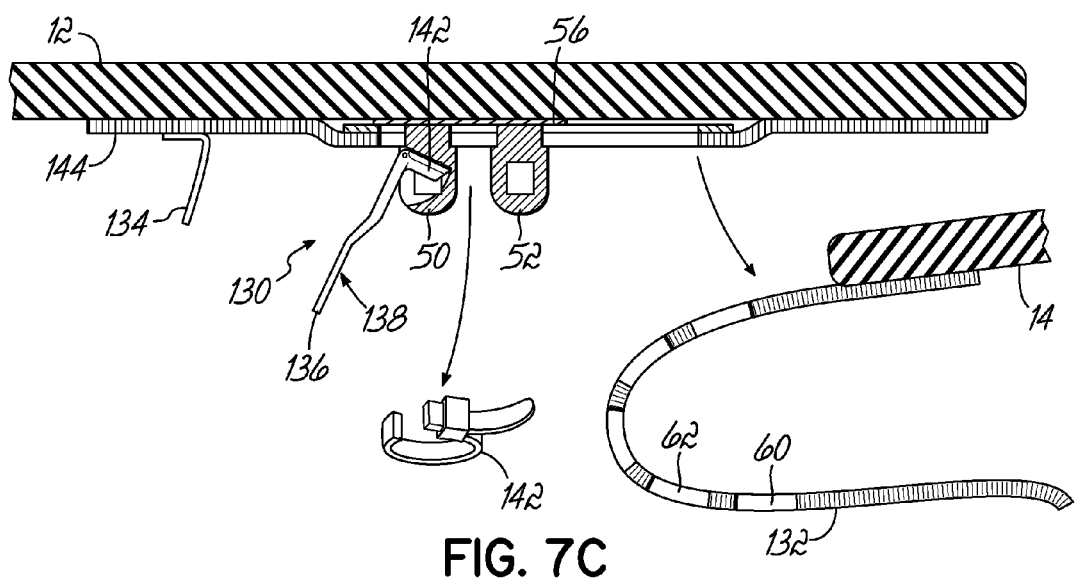

FIGS. 7A-7C illustrate another aspect of the invention in the form of an integrated cutting mechanism 130 associated with the lock system of the collar. In this regard, when the strap 132 is partially lifted and a second underlying cover 134 is also lifted, this exposes a lever portion 136 of a cutter 138. Cover 134, for example, may be comprised of a tag similar to a tag or tags 32 as described above, i.e., an "off-time" tag or tags. This would require that the healthcare worker remove the tag 134 prior to using the cutter 138, as described below, and prompt the worker to fill out the required information on the tag 134 for placement in the patient's chart or other record-keeping purposes. The tag 134 may take other forms as well. Pivoting the lever portion 136 of the cutter 138 away from the collar 10 as shown in FIGS. 7B and 7C causes the blade portion 140 to slice through the lock member 142 (e.g., zip tie) such that the lock member 142 may be removed and the strap 132 fully pulled away from the underlying connector portion 144 as previously described. This integrated cutting mechanism 130 would eliminate the need for a pair of scissors, for example, or other cutting implement to remove the collar 10 from the patient.

Figure 8A:
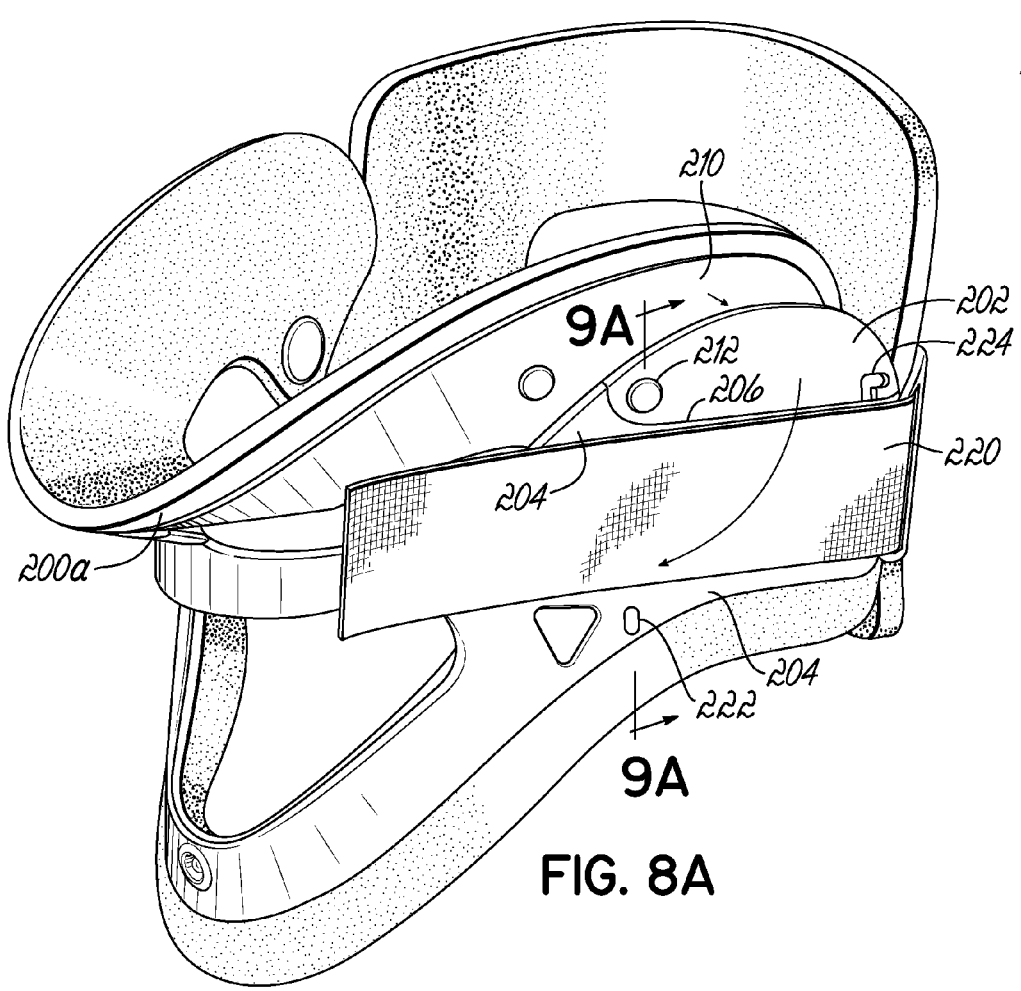
FIG. 8A is a perspective view of a cervical collar including a lock system comprised of a pop-out lever portion that may be used to lock the connector strap of the collar in place.
Figure 8B:
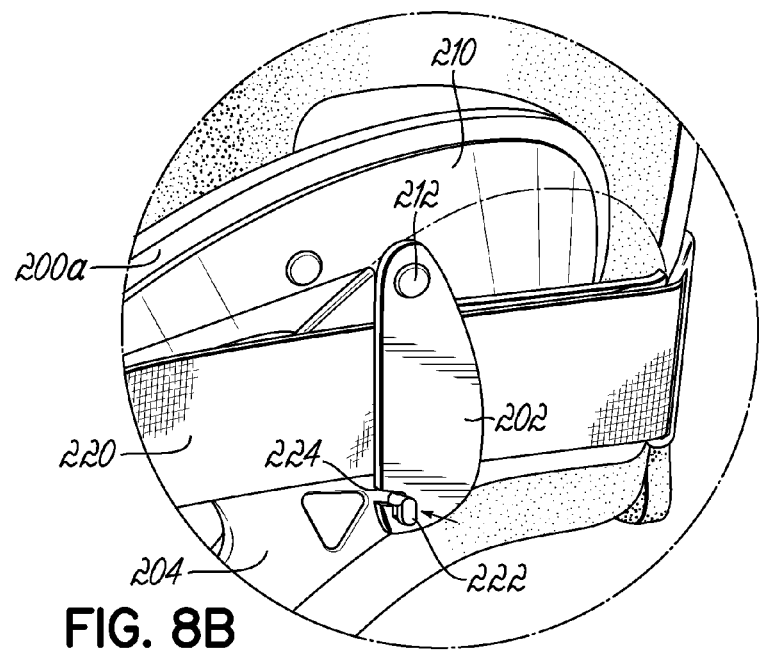
FIG. 8B is an enlarged view of a portion of FIG. 8A showing the lever in a pivoted, locked position.

FIGS. 8A and 8B illustrate one additional form of a lock system on a cervical collar 200 which may otherwise be of a conventional design. In this illustrative embodiment, a pivoting lever arm 202 may be initially secured to a plastic piece 204 of the collar 200 during manufacture, such that the lever arm 202 is temporarily secured to the plastic piece 204 via, for example, a scored or perforated seam 206. One end of the lever arm 202 is also pivotally connected to another plastic piece 210 of the collar 200. As shown in FIG. 8B, the lever arm 202 may be popped outwardly relative to the two plastic pieces 204, 210, for example, and yet remain connected to plastic piece 210 by pivot 212. The pivot 212 itself may also pop-out or move outwardly such that the lever arm 202 may be easily pivoted over a connector strap 220 used to connect the collar 200 in place around a patient's neck. A suitable lock or latch 222 is provided to lock the lever arm 202 in place over the strap 220. This retains the strap 220 and prevents removal of the strap 220 from a support portion 200a of the collar 200 until the lever arm 202 is unlocked and pivoted out of the way.

FIGS. 9A-9C illustrate movement of the lever arm 202 initially outwardly (FIG. 9A) such that the pivot 212 moves outwardly along its axis 212a, and then downwardly in a pivoting motion for engagement with a latch, lock member or any other suitable retaining structure 222. In this example, the latch 222 may be a connector which is initially pushed outwardly as shown in FIG. 9A for engagement with a recess 224 in the lever arm 202 as shown in FIG. 9B and then pushed inwardly as shown in FIG. 9C for firmer engagement with the lever arm 202. To facilitate rotation of the lever back upwardly for removal of the connector strap 220, for example, the latch 222 may be pushed outwardly again as shown in FIG. 9B.

FIG. 10 illustrates another alternative embodiment of a lock system comprising a removable transverse lock member 250, which may be a flexible strap or a more rigid member, secured across a connector strap 252 of the collar 254 using suitable fasteners, such as push-type fasteners 256, 258, sometimes referred to as "Christmas tree" fasteners. These fasteners 256, 258 may be simply pushed into existing holes 260, 262 in one or more plastic pieces of the collar 254. When it is desired to remove the collar 254, the transverse lock member 250 may be removed by pulling the christmas tree fasteners 256, 258 out or pushing them from the opposite side, whichever is easiest.

FIG. 11 illustrates another alternative lock system comprising a flexible strap 270 which may be pre-fixed to the collar 272 and which may be placed over the connector strap 274 of the collar 272 and secured in place by a suitable fastener 276, such as the above-mentioned christmas tree type fastener received in a hole 278 in strap 270 and another hole (not shown) in the underlying collar portion.

As shown in FIGS. 12A and 12B, the lock member or strap 270 in this case may be initially stored in a concealed location behind a plastic piece 280 of the collar 272 and pulled out when needed, as shown in FIG. 12B, for removably fastening over the connector strap 274 of the collar 272.

Figure 13:
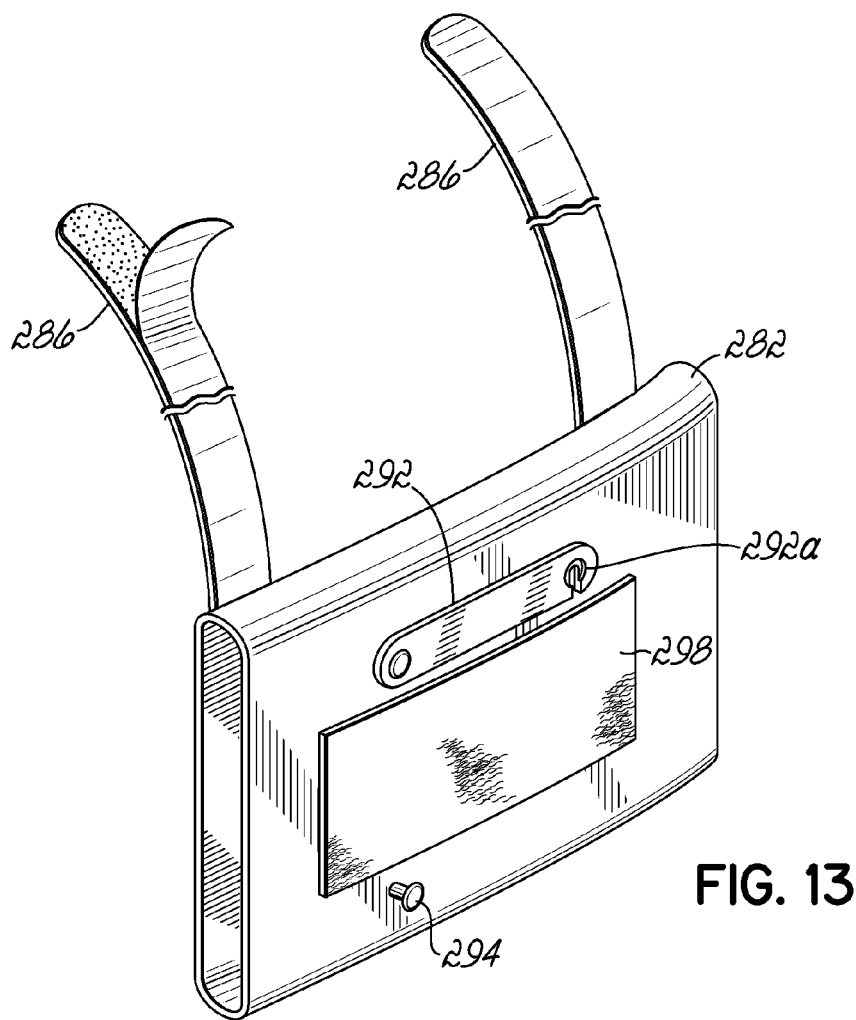
FIGS. 13 and 13A are perspective views showing aftermarket versions of lock systems that may be used in conjunction with conventional collars.
Figure 13A:
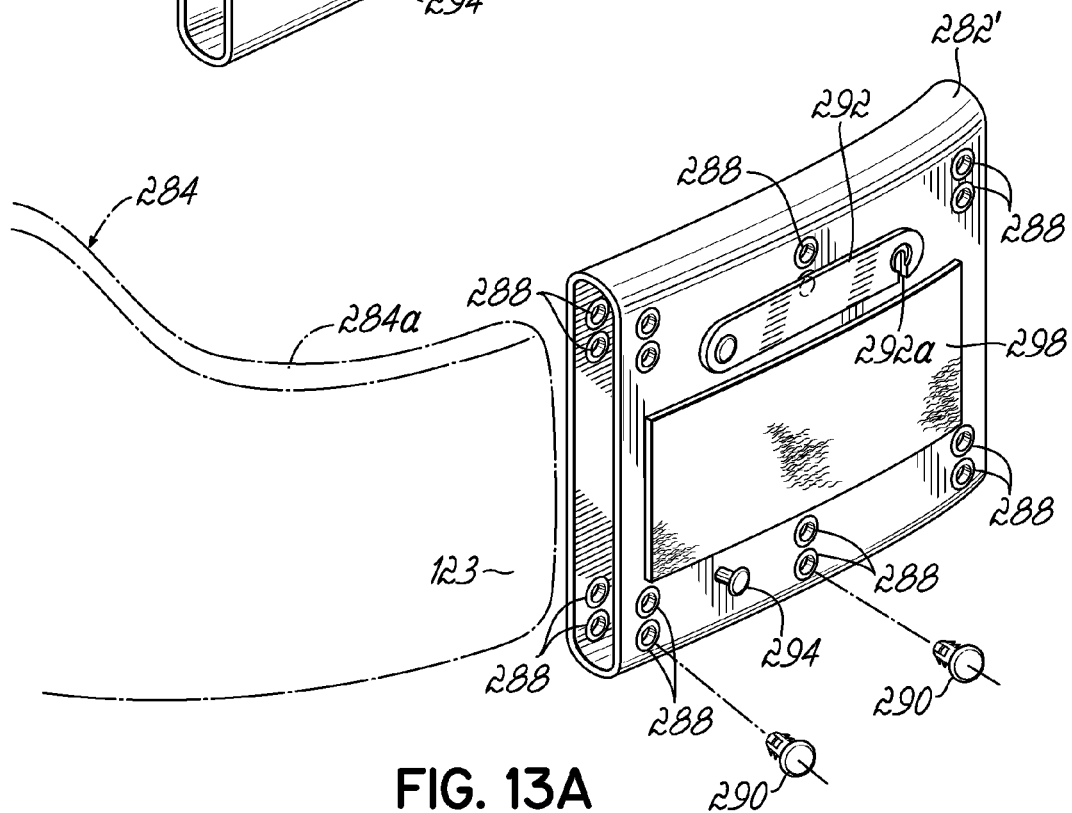

FIGS. 13 and 13A illustrate additional alternative embodiments of a lock system which may comprise a sock or tubular-type structure 282, 282' placed over the end 284a of any existing conventional collar 284 allowing the lock system to be supplied and used as an aftermarket item. The sock 282 may be suitably secured on the end 284a of the collar 284 with adhesive Velcro or other types of straps 286, as shown, or another type of retaining structure may be used on the collar and/or sock or tubular member 282 itself. Another alternative is shown in FIG. 13A in which reinforced holes 288 are provided to receive push fasteners 290 above and below the collar 284. The sock or tubular member may instead simply be retained by friction or in some other manner. The lock system may comprise any of the lock systems contemplated within the scope of the present invention, however, for purposes of illustration only a pivoting lever arm 292 is shown with engagement structure for mating to a suitable latch or other connector element 294 on the sock 282 for securing the pivoting lever arm 292 over a connector strap (not shown), for example, retained on an area of hook or loop fastening material 298 fixed to the sock or tubular member 282. It will be appreciated that once the sock or tubular member 282 is suitable secured to the end 284a of the collar 284, it can act as the end of the collar for securing another portion of the collar thereto and for supplying the desired locking system in accordance with the inventive principles. It will also be appreciated that any other combination of features may be provided on sock or tubular member 282 in accordance with the invention, including lock system components and/or identifier or information elements (e.g., tags, etc.).

Figure 14:
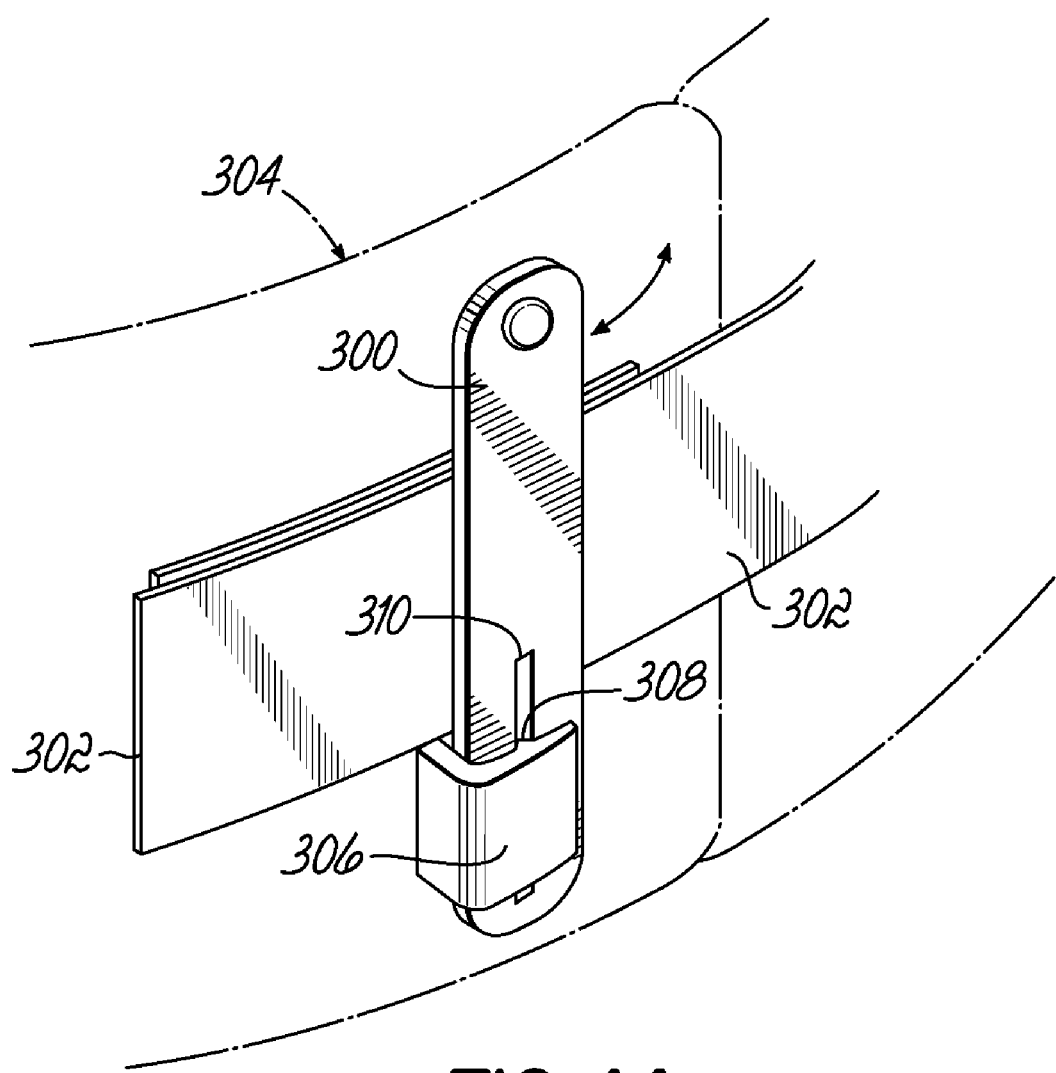
FIG. 14 is an enlarged perspective view illustrating another alternative lock system.

FIG. 14 illustrates another alternative locking system comprising a pivoting lever lock-type bar 300 which may be in another of the forms previously described or otherwise within the scope of the present invention, and which may be pivoted over the connecting strap 302 of the collar 304 and retained in place with a latch 306 by way of a projection 308 on the underside of the latch 306 that is received within a groove or slot 310 in the lever 300. When the lever 300 is pivoted toward the latch 306 the latch 306 may slightly bias away from the lever 300 as the lever 300 slides underneath. The latch 306 will spring back slightly toward the lever 300 when the projection 308 aligns with the slot or groove 310 thereby retaining the lever 300 in place over the connector strap 302 of the collar 304. Inward force on the end 300a of the lever 300 followed by rotation of the lever 300 upwardly will release the lever 300 from the latch 306.

With respect to any of the embodiments described above, any of the various components of the restraint device, such as a cervical collar, may be formed so as to have high visibility to the user. This will assist, for example, in securing the device under adverse conditions such as in dark places or at night. Various high visibility features may be used to achieve this, such as the use of various fluorescent materials, reflective materials, luminescent materials and/or glow in the dark materials. Such high visibility features may be used especially on those smaller components such as straps, lock elements, and identifier or information elements as generally described above so that these elements are more easily seen and manipulated by the user. The use of areas of high visibility will assist with, for example, any securing, fastening, and/or indicating steps associated with the methods described and claimed herein.

While the present invention has been illustrated by a description of various preferred embodiments and while these embodiments has been described in some detail, it is not the intention of the Applicant to restrict or in any way limit the scope of the appended claims to such detail. Additional advantages and modifications will readily appear to those skilled in the art. The various features of the invention may be used alone or in any combination depending on the needs and preferences of the user. This has been a description of the present invention, along with the preferred methods of practicing the present invention as currently known.

However, the invention itself should only be defined by the appended claims, wherein what is claimed is:

1. A cervical collar, comprising:
    a first support portion configured to extend around and support a first portion of the neck of a patient;
    a second support portion configured to extend around and support a second portion of the neck of the patient;
    a first connector portion coupled with the first support portion;
    a second connector portion coupled with the second support portion, said first and second connector portions having respective first and second coupling members capable of being selectively connected together to secure the first and second support portions around the first and second portions of the neck of the patient and disconnected to release the first and second support portions from around the first and second portions of the neck of the patient; and
    an information element operatively coupled to at least one of the first and second support portions, said information element including a machine-readable element.

2. The cervical collar of claim 1, wherein the machine-readable element further comprises a bar code element, an RFID element or a fingerprint patch.

3. The cervical collar of claim 1, wherein at least one of the first support portion, second support portion, first connector portion, second connector portion, or the information element is formed so as to have high visibility to the user.

4. The cervical collar of claim 3, wherein the high visibility is achieved using at least one material selected from the group consisting of: fluorescent materials, reflective materials, luminescent materials and glow-in-the-dark materials.

5. A method of attaching a cervical collar to a patient, comprising:
    securing a first support portion of the cervical collar around a first portion of the neck of a patient;
    securing a second support portion of the cervical collar around a second portion of the neck of the patient;
    fastening a first connector portion coupled with the first support portion to a second connector portion coupled with the second support portion to securely couple the first and second support portions to the neck of the patient thereby securely immobilizing the neck of the patient; and
    reading information from a machine-readable information element associated with the collar.

6. The method of claim 5, further comprising:
    using an area of high visibility on the collar to assist with at least one of the securing, fastening and indicating steps.

7. The method of claim 5, wherein reading information further comprises:
    reading information from an electronic element.

8. The method of claim 7, wherein reading information further comprises:
    reading information from a bar code element.

9. The method of claim 7, wherein reading information further comprises:
    reading information from an RFID.

10. The method of claim 7, wherein reading information further comprises:
    reading information from a fingerprint patch.

11. A restraint device for a person, the device comprising:
    a first restraint portion configured to extend around a first portion of the person;
    a second restraint portion configured to extend around a second portion of the person;
    a first connector portion coupled with the first restraint portion;
    a second connector portion coupled with the second restraint portion, said first and second connector portions having respective first and second coupling members capable of being selectively connected together to secure the first and second restraint portions around the first and second portions of the person to thereby provide a restraint on the person; and
    an information element operatively coupled to at least one of the first and second restraint portions, said information element including a machine-readable element.

12. The cervical collar of claim 11, wherein the machine-readable element further comprises a bar code element, an RFID element or a fingerprint patch.

13. The cervical collar of claim 11, wherein at least one of the first support portion, second support portion, first connector portion, second connector portion, or the information element is formed so as to have high visibility to the user.

14. The cervical collar of claim 13, wherein the high visibility is achieved using at least one material selected from the group consisting of: fluorescent materials, reflective materials, luminescent materials and glow-in-the-dark materials.

15. A method of attaching a restraint device to a person, comprising:
    securing a first restraint portion of the device around a first portion of the person;
    securing a second restraint portion of the device around a second portion of the person;
    fastening a first connector portion coupled with the first restraint portion to a second connector portion coupled with the second restraint portion to securely couple the first and second restraint portions to the person thereby securely restraining at least part of the person; and
    reading information from a machine-readable information element associated with the device.

16. The restraint device of claim 15, wherein the information element is configured to transmit information related to a location of the person.

17. The restraint device of claim 15, wherein the information element is further configured to record information related to the person.

18. The restraint device of claim 15, wherein the information element transmits information by radio frequency signals.

19. The method of claim 15, wherein reading information further comprises:
    reading information from an electronic element.

20. The method of claim 15, wherein reading information further comprises:
reading information from a bar code element.

21. The method of claim 15, wherein reading information further comprises:
reading information from an RFID.

22. The method of claim 15, wherein reading information further comprises:
reading information from a fingerprint patch.

* * * * *